United States Patent
Udipi et al.

(10) Patent No.: US 6,918,929 B2
(45) Date of Patent: Jul. 19, 2005

(54) DRUG-POLYMER COATED STENT WITH PEGYLATED STYRENIC BLOCK COPOLYMERS

(75) Inventors: Kishore Udipi, Santa Rosa, CA (US); Peiwen Cheng, Santa Rosa, CA (US); Kaushik Patel, Windsor, CA (US); Rangarajan Sundar, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 151 days.

(21) Appl. No.: 10/351,156

(22) Filed: Jan. 24, 2003

(65) Prior Publication Data

US 2004/0148003 A1 Jul. 29, 2004

(51) Int. Cl.$^7$ .................................................. A61F 2/06
(52) U.S. Cl. .................... 623/1.42; 623/1.46; 427/2.25
(58) Field of Search ............................. 623/1.42–1.46; 427/2.1–2.31

(56) References Cited

U.S. PATENT DOCUMENTS

| | | |
|---|---|---|
| 4,196,065 A | 4/1980 | Gaussens et al. |
| 4,929,510 A | 5/1990 | Ruckenstein et al. |
| 6,214,901 B1 | 4/2001 | Chudzik et al. |
| 6,270,788 B1 | 8/2001 | Koulik et al. |
| 6,517,889 B1 | 2/2003 | Jayaraman ............... 427/2.24 |
| 2002/0055769 A1 | 5/2002 | Wang ....................... 623/1.13 |

FOREIGN PATENT DOCUMENTS

| | | |
|---|---|---|
| EP | 0970711 | 1/2000 |
| WO | WO 00/32255 A1 | 6/2000 |

*Primary Examiner*—Thomas C. Barrett

(57) ABSTRACT

The present invention provides a system for treating a vascular condition, including a catheter, a stent coupled to the catheter, a drug-polymer coating on the stent including a grafted styrenic block copolymer, and at least one bioactive drug dispersed within the drug-polymer coating.

36 Claims, 6 Drawing Sheets

FIG. 6

DRUG-POLYMER COATED STENT WITH PEGYLATED STYRENIC BLOCK COPOLYMERS

FIELD OF THE INVENTION

This invention relates generally to biomedical stents. More specifically, the invention relates to a drug-polymer coating comprising a pegylated styrenic block copolymer with a dispersed bioactive drug on an endovascular stent for in vivo, timed-release drug delivery.

BACKGROUND OF THE INVENTION

Stenting procedures have had major impact on the field of interventional cardiology and endovascular surgery. Yet, in-stent restenosis and the increasing number of stent-induced lesions and neointimal formation that parallel the number of surgical procedures taint the success of stenting procedures. Much medical research and development in the last decade have been dedicated to stents, and in the most recent years, to drug-eluting coatings for stents. The efficacy of vascular stents is potentially increased by the addition of stent coatings that contain pharmaceutical drugs. These drugs may be released from the coating while in the body, delivering their patent effects at the site where they are most needed. Thus, the localized levels of the medications can be elevated, and therefore potentially more effective than orally- or intravenously-delivered drugs that distribute throughout the body, the latter which may have little effect on the impacted area, or which may be expelled rapidly from the body without achieving their pharmaceutical intent. Furthermore, drugs released from tailored stent coatings may have controlled, timed-release qualities, eluting their bioactive agents over hours, weeks or even months.

Several classes of drug-polymer chemistries have been explored for use in stent coatings as found in current art. A composition with a bioactive agent for coating the surface of a medical device based on poly (alkyl)(meth)acrylate and poly(ethyline-co-vinyl acetate) is described in "Bioactive Agent Release Coating," Chudzik, et al., U.S. Pat. No. 6,214,901, issued Apr. 10, 2001. A composite polymer coating with a bioactive agent and a barrier coating formed in situ by a low energy plasma polymerization of a monomer gas is described in "Polymeric Coatings with Controlled Delivery of Active Agents," K. R. Kamath, publication WO 00/32255, published Jun. 8, 2000. A polymeric coating for an implantable medical article based on hydrophobic methacrylate and acrylate monomers, a functional monomer having pendant chemically reactive amino groups capable of forming covalent bonds with biologically active compounds, and a hydrophilic monomer wherein a biomolecule is coupled to the coated surface, is presented in "Implantable Medical Device," E. Koulik, et al., U.S. Pat. No. 6,270,788, issued Aug. 7, 2001. Use of block copolymers on a hydrophobic polymer substrate is described in "Biocompatible Polymer Articles," E. Ruckenstein, et al., U.S. Pat. No. 4,929,510, issued May 29, 1990. A method for the columetic inclusion and grafting of hydrophilic compounds in a hydrophobic substrate using an irradiation means is described in "Hydrophobic Substrate with Grafted Hydrophilic Inclusions," G. Gaussens, et al., U.S. Pat. No. 4,196,065, issued Apr. 1, 1980.

In selecting polymers for drug delivery, three important criteria must be met: polymer biocompatibility, satisfactory mechanical properties such as durability and integrity during roll down and expansion of the stent, and correct release profiles for the drugs. Candidate chemistries for drug polymers may result in an excessively rapid elution of an incorporated drug. When a drug is eluted too quickly, it may be ineffective and possibly toxic. If a drug is eluted too slowly, the pharmaceutical intent may remain unfulfilled. Furthermore, incorporation of more than one drug in the same coating can result in a much faster elution rate than a second drug in the same drug polymer, making the controlled delivery of multiple drugs difficult. Even pharmaceutical compounds with nearly the same pharmaceutical effect can have dramatically different elution rates in the same coating chemistry, depending on the formation of the compounds.

Unfortunately, some drug polymers do not provide the mechanical flexibility necessary to be effectively used on a stent. A stent may be deployed by self-expansion or balloon expansion, accompanied by a high level of bending at portions of the stent framework, which can cause cracking, flaking, peeling, or delaminating of many candidate drug polymers while the stent diameter is increased by threefold or more during expansion. The candidate drug polymer may not stick or adhere, or it may elute its pharmacologically active constituents too slowly or too quickly, possibly in a toxic manner. If a drug is eluted too slowly, then its intended effect on the body could be compromised. Furthermore, the coating may fall off, crystallize or melt during preparation and sterilization prior to deployment, further limiting the types of drug polymers acceptable for use on cardiovascular stents.

It is desirable to have a drug-polymer system that can be tailored to provide a desired elution rate for a specific drug. It would be beneficial to have a drug-polymer system that can be tailored to accommodate a variety of drugs for controlled time delivery, while maintaining mechanical integrity during stent deployment. A polymeric system that can be readily altered to control the elution rate of interdispersed bioactive drugs and to control their bioavailability is of further benefit.

It is an object of this invention, therefore, to provide a convenient, flexible and biocompatible polymer chemistry for drug-polymer coatings. It is a further object to provide a system and method for treating heart disease and other vascular conditions, to provide methods of manufacturing drug-polymer coated stents, and to overcome the deficiencies and limitations described above.

SUMMARY OF THE INVENTION

One aspect of the invention provides a system for treating a vascular condition, including a catheter, a stent coupled to the catheter, a drug-polymer coating disposed on the stent, and a bioactive drug dispersed within the drug-polymer coating. The drug-polymer coating includes a pegylated styrenic block copolymer matrix. The pegylated styrenic block copolymer matrix comprises a styrenic block copolymer with polymeric grafts of polyethylene glycol. The pegylated styrenic block copolymer matrix provides a controlled drug-elution characteristic for each interdispersed bioactive drug.

Another aspect of the invention is a method of manufacturing a drug-polymer coated stent comprising forming a pegylated styrenic block copolymer solution, forming polymeric grafts of polyethylene glycol along the styrenic block copolymer, mixing at least one bioactive agent in the solution to form a drug-polymer solution, applying the drug-polymer solution onto a stent framework, and drying the drug-polymer solution.

Another aspect of the invention provides a drug-polymer coated stent, comprising a stent framework and a drug-polymer coating disposed on the stent framework, wherein the drug-polymer coating includes a styrenic block copolymer grafted with polyethylene glycol and a bioactive drug dispersed within the drug-polymer coating. The chain length of the block copolymer, the chain length of the polyethylene glycol grafts, and the polyethylene glycol graft density are based on a predetermined elution rate of the bioactive drug.

Another aspect of the invention is a method for treating a vascular condition. A drug-polymer coated stent is inserted within the body, wherein the drug-polymer coated stent includes a bioactive agent and a styrenic block copolymer grafted with polyethylene glycol. The elution rate of the bioactive agent into the body is controlled in part by the grafted styrenic block copolymer. The grafted styrenic block copolymer is selected based on a predetermined elution rate of the bioactive agent.

BRIEF DESCRIPTION OF THE DRAWINGS

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings, wherein:

DETAILED DESCRIPTION OF THE PRESENTLY PREFERRED EMBODIMENTS

In one embodiment of the present invention, modified styrenic block copolymers provide tailored drug-release attributes for drug-polymer coated stents. The modified styrenic block copolymers are combined with interdispersed bioactive agents and used as coatings on vascular stents and other blood-contacting implements. The modified copolymers are mixed with one or more pharmaceutical drugs, the copolymer modifications controlling the elution rate of the drugs from the coated stent into the body.

Styrenic block copolymers such as Kraton® resins are thermoplastic elastomers with styrene end blocks and saturated or unsaturated mid-blocks. In terms of molecular structure, Kraton® resins are anionically polymerized block copolymers with hydrophobic and hydrophilic phase separation properties. Styrenic block copolymers such as Kraton-G® or Kraton-D® provide coatings with good overall property balance, particularly with respect to durability and drug elution. Kraton® polymers such as Kraton-G® and Kraton-D® are manufactured by Kraton Polymers® of Houston, Tex. Kraton-G® polymers have a saturated mid-block such as an ethylene and butylene random copolymer (SEBS) or an ethylene and propylene chain (SEPS). Kraton-D® polymers have an unsaturated rubbery mid-block such as butadiene (SBS) or isoprene (SIS). The rubbery mid-blocks offer good impact resistance properties at low and ambient temperatures. The relatively low glass transition temperature (Tg) also gives better adhesive properties and relatively fast drug release. In addition, Kraton® resins have very good compatibility with a wide range of polymers to allow combinations of properties that could not be achieved otherwise.

Styrenic block copolymers may be modified with bio-friendly polymers like polyethylene glycol (PEG). The PEG component offers a highly biocompatible system to the tissues and cells surrounding an implanted stent. Grafts of polyethylene glycol may be attached along the styrenic block copolymer. The grafts provide a pronounced hydrophilic characteristic. Pharmaceutical compounds with a similar hydrophilic characteristic are readily attached to the hydrophilic grafts. Increased loading of such compounds occurs with increased density of polyethylene glycol grafts, resulting in higher concentrations of the drug along the grafts. Increased loading of such compounds also occurs with increased length of the grafts.

The double bond in the rubbery mid-block of Kraton-D® can be a result of hydroxylation, and the hydroxyl functional group can be further reacted with functional polymers to form graft polymers. When grafting with a biocompatible polymer such as polyethylene glycol, a further phase separation system results. The hydrocarbon component of the backbone provides flexibility and adhesion to metal. In addition, the backbone of the styrenic block copolymer can be an effective matrix for hydrophobic drug loading and releasing.

By tailoring the grafted styrenic block copolymer, the concentration, distribution profile, and elution rates of bioactive agents or drugs can be controlled. The elution rate of the bioactive drug is usually predetermined based on chain length of the styrenic block copolymer, the chain length of the polyethylene glycol grafts, the polyethylene glycol graft density, and the structure of the bioactive agents or drugs, among others. In an exemplary embodiment of the current invention, the grafted styrenic block copolymers are oriented on a stent framework such that the predominantly hydrophilic grafts are outwardly directed towards the surface of the stent coating, whereas the predominantly hydrophobic main chain is nearer to the stent framework. This phase separation configuration typically results in higher elution rates for hydrophilic drugs near the periphery of the coated stent, and slower elution rates for more hydrophobic drugs near the metal-coating interface.

In cases where the grafted styrenic block copolymer provides inadequate adhesion to the underlying metallic stent framework, an intermediate primer coating or adhesion layer is often incorporated between the drug-polymer coating and the stent framework.

One aspect of the present invention is a system for treating heart disease, various cardiovascular ailments, and other vascular conditions using catheter-deployed endovascular stents with tailored polymeric coatings for controlling the timed-release properties of interdispersed bioactive agents and drugs. Treating vascular conditions refers to the prevention or correction of various ailments and deficiencies associated with the cardiovascular system, urinogenital systems, biliary conduits, abdominal passageways and other biological vessels within the body.

Figure 1:
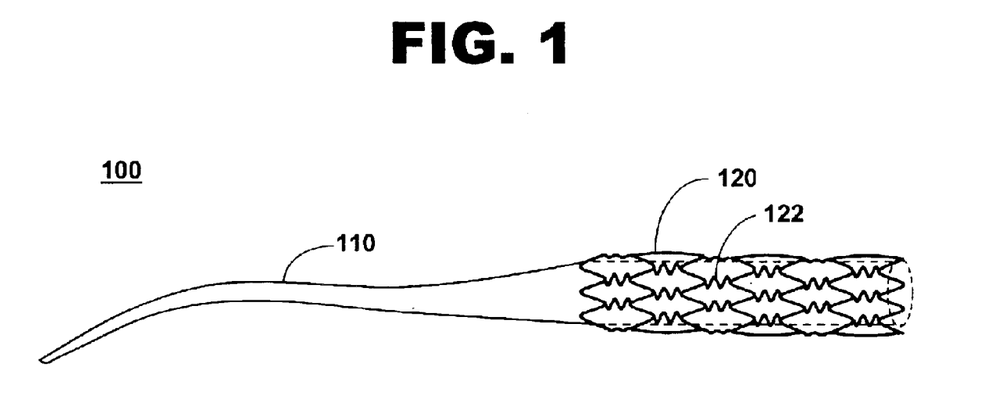
FIG. 1 is an illustration of one embodiment of a system for treating a vascular condition including a catheter, a stent, and a drug-polymer coating including at least one bioactive agent disposed on the stent, in accordance with the current invention.

One embodiment of the system for treating a vascular condition, in accordance with the present invention, is illustrated in FIG. 1 at 100. In this embodiment, vascular condition treatment system 100 includes a catheter 110, a stent 120 coupled to the catheter, and a drug-polymer coating 122 on the stent or stent framework. Drug-polymer coating 122 includes a grafted styrenic block copolymer, and one or more bioactive agents dispersed throughout the coating. The bioactive agent is a pharmacologically active drug or bioactive compound. The grafted styrenic block copolymer controls the elution rates of the bioactive agents, and provides a controlled drug-elution characteristic for each bioactive agent or drug. Drug elution refers to the transfer of the bioactive agent out from drug-polymer coating 122. The elution is determined as the total amount of bioactive agent excreted out of drug-polymer coating 122, typically measured in units of weight such as micrograms, or in weight per peripheral area of the stent. In one embodiment, the polymeric coating includes between 0.5 percent and 50 percent of the bioactive agent of drug by weight.

Upon insertion of catheter 110 and stent 120 with drug-polymer coating 122 into a directed vascular region of a human body, stent 120 may be expanded by applying pressure to a suitable balloon inside the stent, or by retracting a sheath to allow expansion of a self-expanding stent. Balloon deployment of stents and self-expanding stents are well known in the art. Catheter 110 may include the balloon used to expand stent 120. Catheter 110 may include a sheath that retracts to allow expansion of a self-expanding stent.

Figure 2:
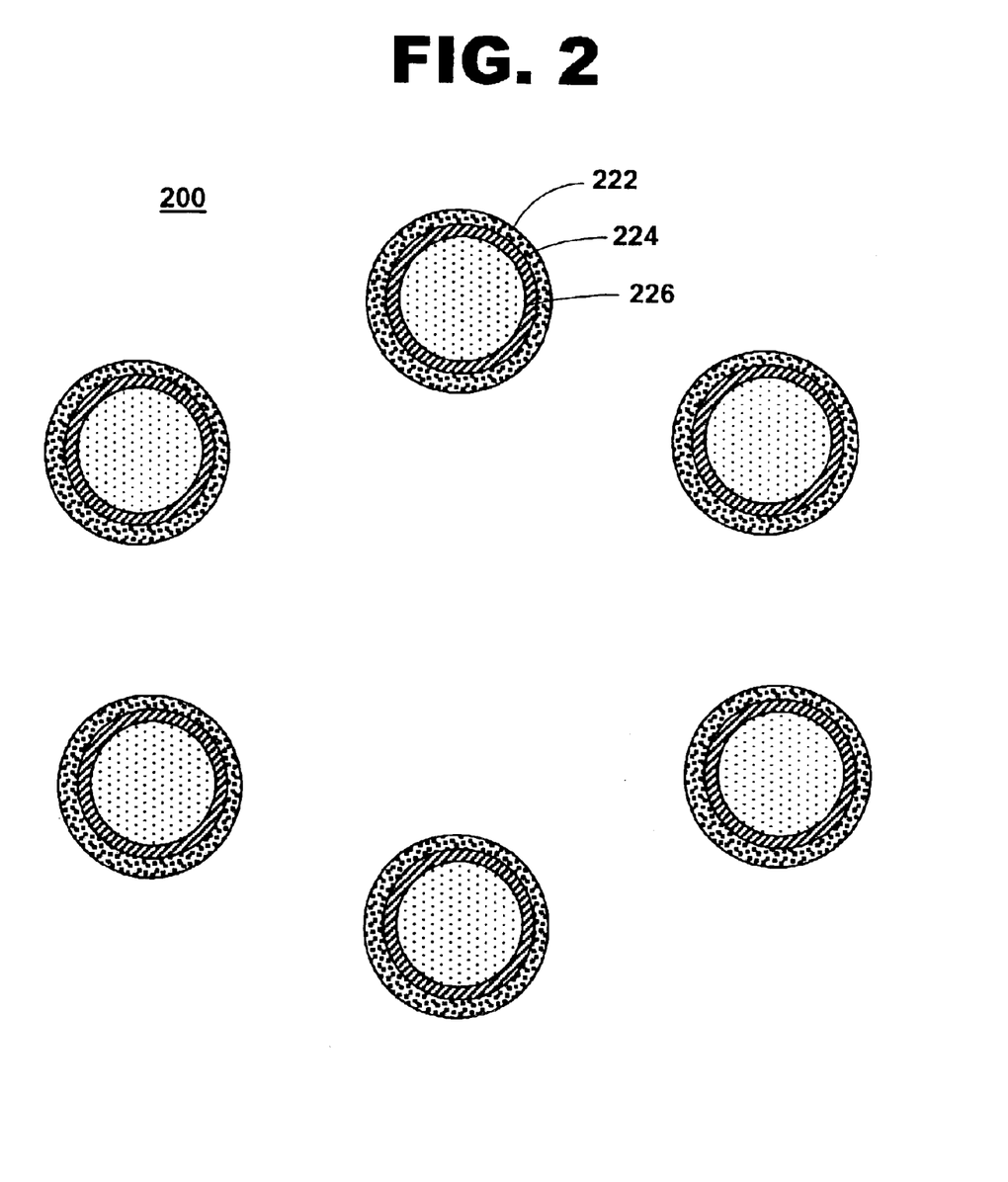
FIG. 2 is a cross-sectional view of one embodiment of a drug-polymer coated stent, in accordance with the current invention.

FIG. 2 shows an illustration of a stent cross-section containing a drug-polymer coating on the stent surface, in accordance with the present invention at 200. Drug-polymer coated stent 200 includes a drug-polymer coating 222 and an optional primer coating 224 disposed on a stent framework 226. Drug-polymer coating 222 includes a grafted styrenic block copolymer forming a polymeric matrix, with a bioactive drug dispersed within the matrix. Drug-polymer coating 222 may contain one or more pharmaceutical drugs or bioactive agents. Drug-polymer coating 222 may contain a polymeric matrix in which one or more bioactive agents are interdispersed.

"Stent framework 226 typically includes a metallic or polymeric base. The metallic base comprises a metal such as stainless steel, nitinol, tantalum, a nonmagnetic nickel-cobalt-chromium-molybdenum alloy such as MP35 N®[alloy], platinum, titanium, a suitable biocompatible alloy, a suitable biocompatible material, or any combination thereof. The polymeric base material is any suitable polymer for biomedical stent applications, as is known in the art."

Exemplary drug-polymer coated stent 200 includes one or more polymeric coatings on stent framework 226. A barrier coating, adhesive coating or primer coating 224 can be positioned between drug-polymer coating 222 and stent framework 226 to improve the adhesion of the drug-polymer coating and its durability. Primer coating 224 may be a polymeric material or any material that adheres well to the underlying stent, particularly a metallic stent. Primer coating 224 is selected to adhere well to the stent and to be readily coated with another polymeric material such as the drug-polymer coating. Primer coating 224 may be any suitable polymeric primer material such as parylene, polyurethane, phenoxy, epoxy, polyimide, polysulfone, or pellathane.

Drug-polymer coating 222 may have a predominantly hydrophobic characteristic along the backbone of the block copolymer to improve metal adhesion and, in some cases, to enhance the elution of embedded bioactive material. Drug-polymer coating 222 may also have a hydrophilic characteristic associated with the grafts attached to the backbone. A relatively hydrophobic characteristic usually slows or mitigates the elution of the bioactive agents and polymeric material into the body, whereas a relatively hydrophilic characteristic typically has a high elution rate of the bioactive agents. The combination of hydrophobic and hydrophilic aspects of the grafted styrenic block copolymer coating provides controllable elution rates for bioactive material within the drug-polymer coating.

Drug-polymer coating 222 includes one or more bioactive drugs or agents. The bioactive agents provide treatment or prevention of one or more conditions including coronary restenosis, cardiovascular restenosis, angiographic restenosis, arteriosclerosis, hyperplasia, and other diseases and conditions. For example, the bioactive agent can be selected to inhibit or prevent vascular restenosis, a condition corresponding to a narrowing or constriction of the diameter of the bodily lumen where the stent is placed. In one embodiment, the bioactive drug comprises an antirestenotic agent. In another embodiment, the bioactive drug comprises a bioactive agent such as an antisense agent, an antineoplastic agent, an antiproliferative agent, an antithrombogenic agent, an anticoagulant, an antiplatelet agent, an antibiotic, an anti-inflammatory agent, a steroid, a gene therapy agent, a therapeutic substance, an organic drug, a pharmaceutical compound, a recombinant DNA product, a recombinant RNA product, a collagen, a collagenic derivative, a protein, a protein analog, a saccharide, and a saccharide derivative. In another embodiment, drug-polymer coating 222 includes a combination of pharmaceutical drugs.

A number of pharmaceutical drugs have the potential to be used in drug-polymer coatings. For example, an antirestenotic agent such as rapamycin or rapamycin derivatives prevents or reduces the recurrence of narrowing and blockage of the bodily vessel. An antisense drug works at the genetic level to interrupt the process by which disease-causing proteins are produced. An antineoplastic agent is typically used to prevent, kill, or block the growth and spread of cancer cells in the vicinity of the stent. An antiproliferative agent may prevent or stop targeted cells or cell types from growing. An antithrombogenic agent actively retards blood clot formation. An anticoagulant often delays or prevents blood coagulation with anticoagulant therapy, using compounds such as heparin and coumarins. An antiplatelet agent may be used to act upon blood platelets, inhibiting their function in blood coagulation. An antibiotic is frequently employed to kill or inhibit the growth of microorganisms and to combat disease and infection. An anti-inflammatory agent such as dexamethasone can be used to counteract or reduce inflammation in the vicinity of the stent. At times, a steroid is used to reduce scar tissue in proximity to an implanted stent. A gene therapy agent may be capable of changing the expression of a person's genes to treat, cure or ultimately prevent disease.

By definition, a bioactive agent is any therapeutic substance that provides prevention or treatment of disease or disorders. An organic drug is any small-molecule therapeutic material. A pharmaceutical compound is any compound that provides a therapeutic effect. A recombinant DNA product or a recombinant RNA product includes altered DNA or RNA genetic material. Bioactive agents of pharmaceutical value may also include collagen and other proteins, saccharides, and their derivatives. The molecular weight of the bioactive agent typically ranges from 200 to 60,000 Dalton and above.

Drug-polymer coating 222 elutes at least one bioactive agent. Drug-polymer coating 222 may include and elute multiple bioactive agents. Drug-polymer coating 222 can be tailored to control the elution of one or more bioactive agents primarily by diffusion processes. In some cases, a portion of the polymeric coating is absorbed into the body to release bioactive agents from within the coating.

Drug-polymer coating 222 contains a grafted styrenic block copolymer wherein the grafted styrenic block copolymer comprises a styrenic block copolymer grafted with polyethylene glycol. The structure of the grafted styrenic block copolymer controls the elution rate of the bioactive drugs, and the structure of the grafted styrenic block copolymer may be selected to achieve predetermined elution rates of various bioactive agents and drugs interdispersed within the polymer-drug coating. Modification of the styrenic block copolymer allows, for example, rapid delivery of a pharmacologically active drug or bioactive agent within twenty-four hours of surgery, with a slower, steady delivery of a second bioactive agent over the next three to six months.

Drug-polymer coating 222 may include a plurality of drugs, each drug having a predetermined elution rate. The structure of the pegylated styrenic block copolymer may be selected to elute the drugs at the predetermined elution rates. The pegylated styrenic block copolymer matrix disposed on the stent framework may have both a hydrophobic and a hydrophilic characteristic, the hydrophobic characteristic being more pronounced adjacent to the stent framework, and the hydrophilic characteristic being more pronounced adjacent to the outer surface of the drug-polymer coating. In one embodiment, a first bioactive drug having a hydrophobic characteristic is concentrated adjacent the stent framework, and a second bioactive drug having a hydrophilic characteristic is concentrated adjacent the outer surface of the drug-polymer coating. For example, the first bioactive drug may comprise an antirestenotic drug such as rapamycin or a rapamycin derivative. The second bioactive drug may comprise an anti-inflammatory drug such as dexamethosone.

Figure 3:
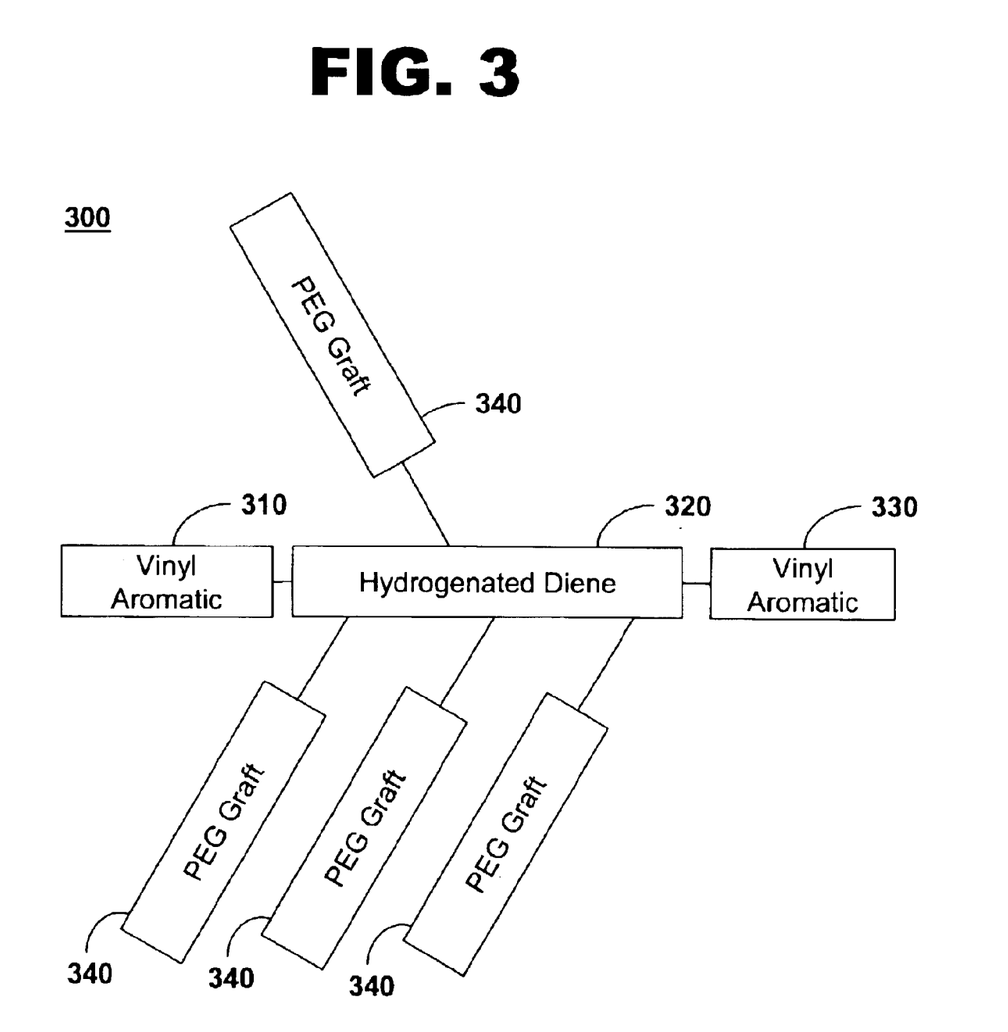
FIG. 3 is a schematic illustration of a grafted styrenic block copolymer, in accordance with the current invention.

FIG. 3 shows a schematic illustration of a grafted styrenic block copolymer, in accordance with the present invention at 300. Grafted styrenic block copolymer 300 has a styrenic block polymer main chain with two end-blocks 310 and 330, a mid-block 320, and polymeric grafts 340. End-blocks 310 and 330 are vinyl aromatics such as styrene, and mid-block 320 comprises a hydrogenated diene. The hydrogenated diene can be saturated or unsaturated. Grafted styrenic block copolymer 300 may comprise a main chain of styrene-ethylene/butylene-styrene, where the ethylene/butylene is a random copolymer linear chain. Another example of a grafted styrenic block copolymer with a saturated mid-block along the polymer main chain is styrene-ethylene/propylene-styrene, where the ethylene/propylene represents a linear copolymer chain between two end-blocks of styrene. Grafted styrenic block copolymer 300 may comprise vinyl aromatic end-blocks 310 and 330 with an unsaturated diene along the main chain, such as styrene-butadiene-styrene or styrene-isoprene-styrene. The styrenic block copolymer may have a molecular weight between 200 Daltons and 200,000 Daltons, depending on the length of the block copolymer and the desired elution characteristics.

Grafted styrenic block copolymer 300 includes one or more side grafts attached along the main chain. The grafts are formed from polyethylene glycol, and may have a molecular weight between 500 Daltons and 500,000 Daltons depending on the length of the graphs and the desired elution characteristics.

The grafted styrenic block copolymer disposed on the stent framework provides a controlled drug-elution characteristic, with a higher density of grafting corresponding to a higher or lower drug-elution rate depending on the particular pharmaceutical compound. The length of the main chain also impacts the drug elution rate and the relative amount of drug loading along the main chain, particularly with respect to pharmaceutical compounds with a lesser hydrophilic characteristic or a predominantly hydrophobic nature.

Figure 4:
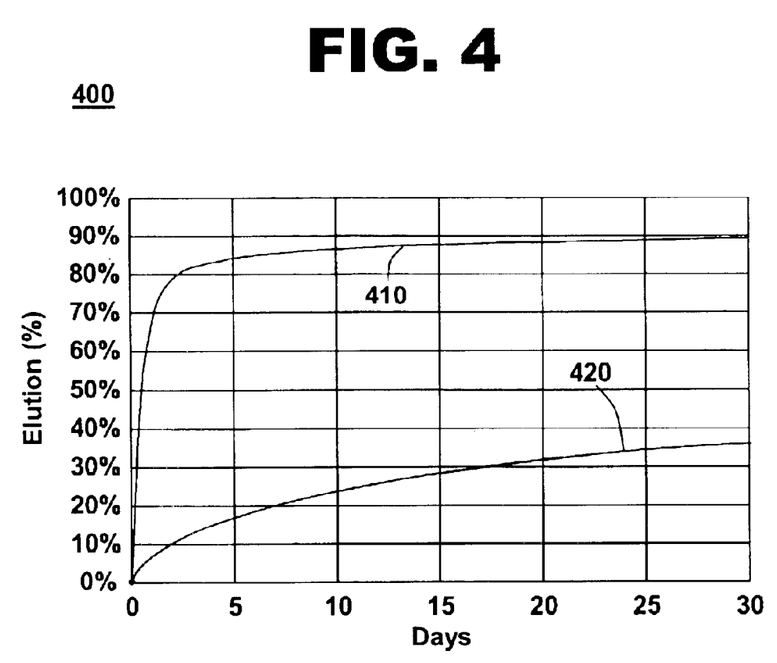
FIG. 4 is a graphical illustration of drug elution from a drug-polymer coated stent with two bioactive agents, in accordance with the current invention.

FIG. 4 shows a graphical illustration of the elution of two bioactive agents from a drug-polymer coated stent, in accordance with the present invention at 400. Elution graph 400 shows the elution of two drugs from a drug-polymer coated stent as a function of time. The elution of the bioactive agents is indicated as a percentage by weight of total drug dispersed within the stent coating. Typical units used for drug elution include micrograms of drug. Alternatively, they can be normalized to a unit volume with units such as micrograms per cubic centimeter of drug-polymer, or normalized to the periphery area of the stent with units such as micrograms per square centimeter. The elution profile 410 of the first drug shows a high rate of drug delivery over an initial period of two days or so after stent deployment, with minimal drug eluted over the remainder of the month. The elution profile 420 of the second drug shows a slow initial rate of drug delivery, and steady delivery of the drug over an extended period of time. The elution rates of the drugs are determined from a typical elution graph 400 by taking the derivative with respect to time, or by dividing the total amount of drug eluted by the elapsed time since stent deployment. Selection of the appropriate drug, the chain length of the styrenic block copolymer, the chain length of the polyethylene glycol grafts, the polyethylene glycol graft density, and the method of preparation, among others, establish the elution profile of the bioactive agents.

Figure 5:
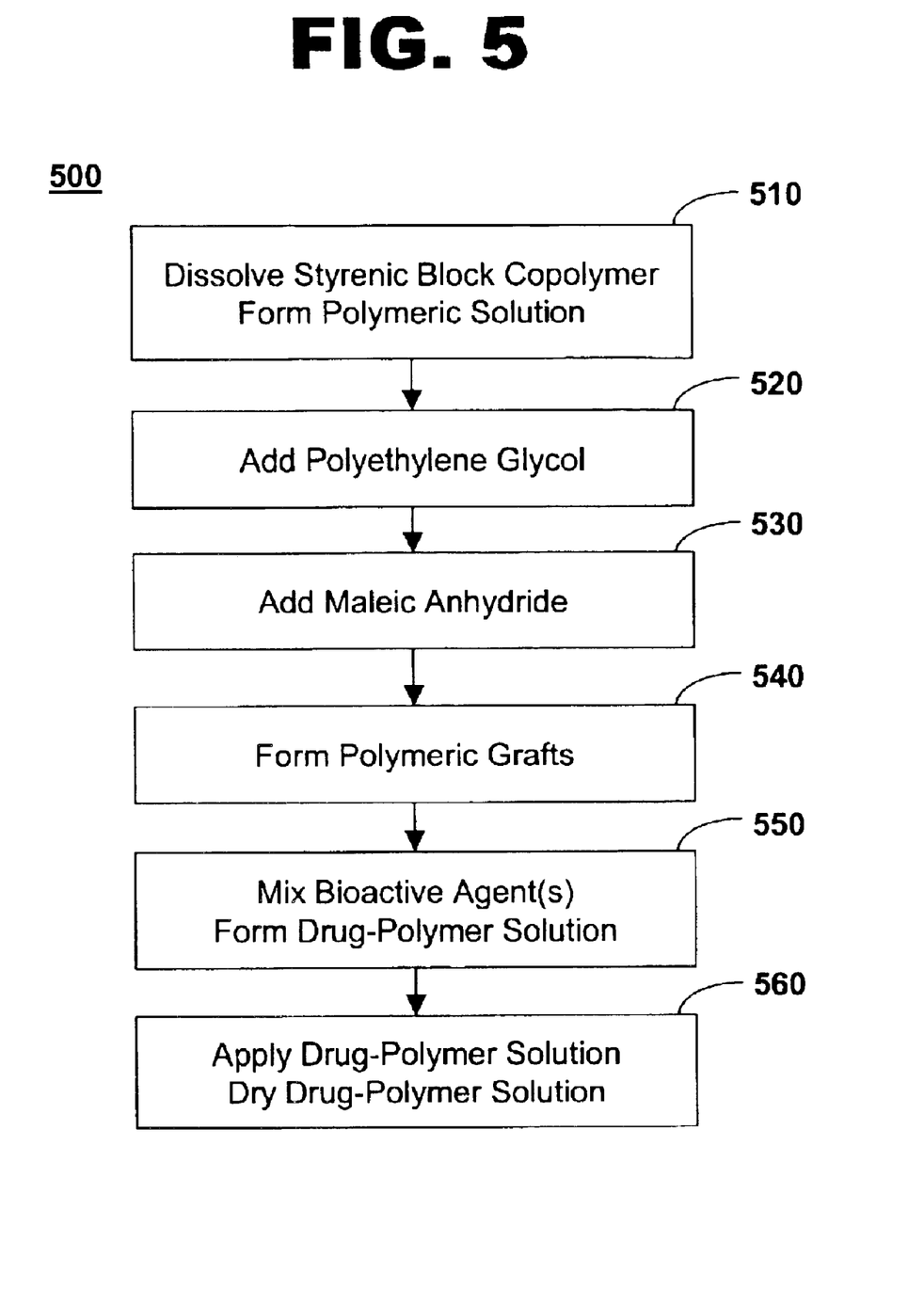
FIG. 5 is a flow diagram of one embodiment of a method of manufacturing a drug-polymer coated stent, in accordance with the current invention.

Another aspect of the current invention is a method of manufacturing a drug-polymer coated stent. FIG. 5 shows a flow diagram of one embodiment of a method of manufacturing a drug-polymer coated stent including a grafted styrenic block copolymer and one or more bioactive agents, in accordance with the present invention at 500. Drug-polymer coated stent manufacturing method 500 comprises steps to form a drug-polymer solution containing the grafted styrenic block copolymers, and one or more drugs or pharmaceutical compounds.

In this embodiment, a styrenic block copolymer such as Kraton-G® or Kraton-D® is dissolved in a pegylated styrenic block copolymer solvent to form a polymeric solution, as seen at block 510. The styrenic block copolymer has a molecular weight, for example, between 200 Daltons and 200,000 Daltons. The solvent may be any suitable organic solvent capable of dissolving the styrenic block copolyer such as chloroform, tetrahydrofuran, methyl chloride, toluene, ethyl acetate, or dioxane.

Polyethylene glycol is added to the polymeric solution to form a polymeric solution of styrenic block copolymer and polyethylene glycol, as seen at block 520. The polyethylene glycol may be added directly to the polymeric solution. Alternatively, the polyethylene glycol may be dissolved in a suitable organic solvent such as chloroform, tetrahydrofuran, methyl chloride, toluene, ethyl acetate or dioxane, and then mixed with the styrenic block copolymer solution to form the polymeric solution. The polyethylene glycol has a molecular weight, for example, between 500 Daltons and 500,000 Daltons. The molecular weight of the polyethylene glycol and the concentration of the polyethylene glycol in solution combine with the molecular weight of the styrenic block copolymer and the concentration of the styrenic block copolymer to provide a controlled drug-elution characteristic, and may be selected to provide a predetermined elution rate for each of the bioactive drugs.

An aliquot of maleic anhydride may be added to the polymeric solution to initiate formation of the polymeric grafts, as seen at block 530. A polymeric initiator such as maleic anhydride may be used to react with the butylene, propylene, or other backbone groups along the styrenic block copolymer to open bond sites for the grafting of the polyethylene glycol.

The polyethylene glycol reacts with the styrenic block copolymer to form polymeric grafts on the main chain, as seen at block 540. The polyethylene glycol grafts may randomly occur along the main chain, or may align themselves preferentially along hydroxyl groups distributed along the main chain.

One or more bioactive agents are mixed with the polymeric solution to form a drug-polymer solution, as seen at block 550. The bioactive agents may be added directly into the polymeric solution and mixed to form the drug-polymer solution. Alternatively, the bioactive agents may be dissolved in a bioactive agent solution comprising a suitable solvent, then mixed with the polymeric solution to form the drug-polymer solution. In either case, a suitable amount of bioactive agent or drug is added to the drug-polymer solution. Sufficient bioactive agents are added to achieve the desired pharmaceutical intent when deployed. The drug constituency within the drug-polymer coating is usually between 0.5 percent and 50 percent of the bioactive drug by weight.

The drug-polymer solution is then applied to the stent framework and dried, as seen at block 560. The drug-polymer solution is applied by using an application technique such as dipping, spraying, painting or brushing. The drug-polymer solution may be dried by evaporating the solvent after application. The drying may be performed at room temperature and under ambient conditions. A nitrogen environment or other controlled environment may also be used. Alternatively, the drug-polymer solution can be dried by evaporating the majority of the solvent at room temperature, and further drying the solution in a vacuum environment between room temperature of about 25 degrees centigrade and 45 degrees centigrade or higher to extract any pockets of solvent buried within the drug-polymer coating.

The thickness of the drug-polymer coating can vary, though is typically between 0.5 microns and 20 microns. Depending on the diameter and length of the stent, the weight of the drug-polymer coating is usually between 50 micrograms and 1500 micrograms for a range of stent sizes. Additional coats may be added to thicken the drug coating or to increase the drug dosage, if needed.

A barrier coating or a primer coating may be disposed on the stent framework prior to coating with the drug-polymer to improve adhesion, particularly to metal stents such as stainless steel. The primer coating is any suitable primer material such as parylene, polyurethane, phenoxy, epoxy, polyimide, polysulfone, pellathane, or a suitable polymeric primer material.

Variants of the method for manufacturing a drug-polymer coated stent can be used, such as mixing the constituents into the same solution, using different solvents for each component, or altering the order of mixing stock solutions of each of the constituents.

Figure 6:
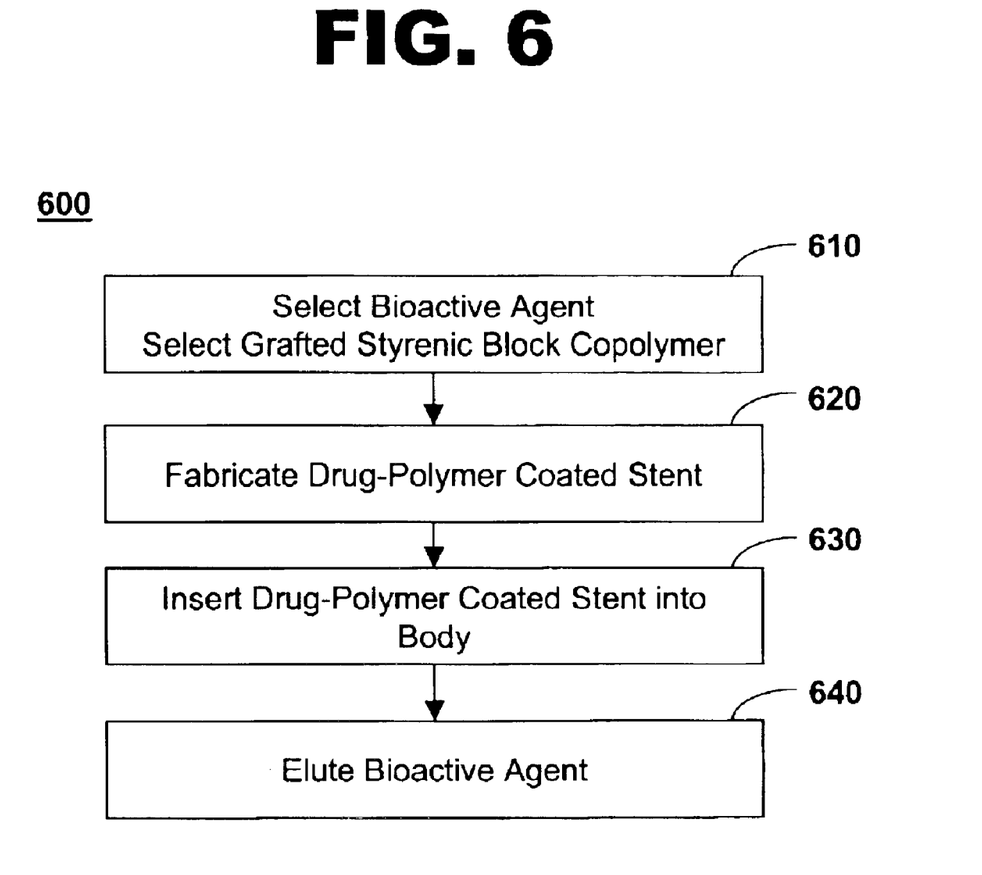
FIG. 6 is a flow diagram of one embodiment of a method of treating a vascular condition, in accordance with the current invention.

Another aspect of the present invention is a method of treating a vascular condition. FIG. 6 shows a flow diagram of one embodiment of a method of treating a vascular condition, in accordance with the present invention at 600.

In this embodiment, one or more bioactive agents or drugs are selected along with the molecular weight of the grafts, the graft density along the main chain, and the molecular weight of the main chain. The structure of the grafted styrenic block copolymer is selected to achieve an intended pharmaceutical intent such as a predetermined elution rate of each bioactive agent, as seen at block 610.

A drug-polymer coated stent is fabricated with the selected grafted styrenic block copolymer and bioactive agents, as seen at block 620. The stent is suitably cleaned, primed with a suitable primer coating if needed, and coated with the drug-polymer coating. The drug-polymer coating includes a bioactive agent and a pegylated styrenic block copolymer. In this exemplary method, the coated stents are reduced in diameter and placed into the distal end of the catheter. The process forms an interference fit, which secures the stent onto the catheter. The catheter with the stent may be placed in a catheter package and sterilized prior to shipping and storing. Sterilization of the stent using conventional means is typically completed before clinical use.

When ready for deployment, the drug-polymer coated stent including the bioactive agents and the grafted styrenic block copolymer is inserted into a vessel of the body, as seen at block 630. The drug-polymer coated stent is inserted typically in a controlled environment such as a catheter lab or hospital. The stent is deployed, for example, by expanding the stent with a balloon or by extracting a sheath to allow a self-expandable stent to enlarge after positioning the stent at the desired location within the body.

Once deployed, the drug-polymer coating elutes the bioactive agents into the body and particularly into the tissue bed surrounding the stent framework, as seen at block 640. The elution rates of the bioactive agents into the body are based on the structure of the grafted styrenic block copolymer, among other factors.

Although the present invention applies to cardiovascular and endovascular stents with timed-release pharmaceutical drugs, the use of grafted styrenic block copolymers in polymer-drug coatings and polymer coatings may be applied to other implantable and blood-contacting biomedical devices such as coated pacemaker leads, microdelivery pumps, feeding and delivery catheters, heart valves, artificial livers and other artificial organs.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A system for treating a vascular condition, comprising:
   a catheter;
   a stent coupled to the catheter, the stent including a stent framework;
   a drug-polymer coating disposed on the stent framework, wherein the drug-polymer coating comprises a pegylated styrenic block copolymer matrix; and a bioactive agent dispersed within the pegylated styrenic block copolymer matrix.

2. The system of claim 1 wherein the catheter includes a balloon used to expand the stent.

3. The system of claim 1 wherein the catheter includes a sheath that retracts to allow expansion of the stent.

4. The system of claim 1 wherein the stent framework comprises a metallic base.

5. The system of claim 4 wherein the metallic base is selected from the group consisting of stainless steel, nitinol, tantalum, a nonmagnetic nickel-cobalt-chromium-molybdenum [MP35N] alloy, platinum, titanium, a suitable biocompatible alloy, a suitable biocompatible material, and a combination thereof.

6. The system of claim 1 wherein the stent framework comprises a polymeric base.

7. The system of claim 1 wherein the pegylated styrenic block copolymer matrix comprises a styrenic block copolymer and polymeric grafts of polyethylene glycol.

8. The system of claim 7 wherein the styrenic block copolymer has a molecular weight between 200 Daltons and 200,000 Daltons.

9. The system of claim 7 wherein the polymeric grafts have a molecular weight between 500 Daltons and 500,000 Daltons.

10. The system of claim 1 wherein the pegylated styrenic block copolymer matrix provides a controlled drug-elution characteristic.

11. The system of claim 1 wherein the drug-polymer coating comprises between 0.5 percent and 50 percent of the bioactive agent by weight.

12. The system of claim 1 wherein the drug-polymer coating has a thickness between 0.5 microns and 20 microns.

13. The system of claim 1 wherein the drug-polymer coating has a weight between 50 micrograms and 1500 micrograms.

14. The system of claim 1 wherein the bioactive agent comprises an antirestenotic drug.

15. The system of claim 1 wherein the bioactive agent is selected from a group consisting of an antisense agent, an antineoplastic agent, an antiproliferative agent, an anti-thrombogenic agent, an anticoagulant, an antiplatelet agent, an antibiotic, an anti-inflammatory agent, a steroid, a gene therapy agent, a therapeutic substance, an organic drug, a pharmaceutical compound, a recombinant DNA product, a recombinant RNA product, a collagen, a collagenic derivative, a protein, a protein analog, a saccharide, and a saccharide derivative.

16. The system of claim 1 wherein the drug-polymer coating comprises a plurality of drugs, each drug having a predetermined elution rate, the pegylated styrenic block copolymer matrix eluting the drugs at the predetermined elution rates.

17. The system of claim 1 wherein the pegylated styrenic block copolymer matrix disposed on the stent framework has a hydrophobic characteristic and a hydrophilic characteristic, the hydrophobic characteristic being more pronounced adjacent the stent framework, and the hydrophilic characteristic being more pronounced adjacent an outer surface of the drug-polymer coating.

18. The system of claim 17 wherein a first bioactive drug having a hydrophobic characteristic is concentrated adjacent the stent framework, and a second bioactive drug having a hydrophilic characteristic is concentrated adjacent the outer surface of the drug-polymer coating.

19. The system of claim 18 wherein the first bioactive drug comprises an antirestenotic drug and the second bioactive drug comprises an anti-inflammatory drug.

20. The system of claim 1 further comprising:
a primer coating disposed on the stent framework between the stent framework and the drug-polymer coating.

21. The system of claim 20 wherein the primer coating is selected from the group consisting of parylene, polyurethane, phenoxy, epoxy, polyimide, polysulfone, pellathane, and a suitable polymeric primer material.

22. A method of manufacturing a drug-polymer coated stent, comprising:
forming a polymeric solution including a styrenic block copolymer and a pegylated styrenic block copolymer solvent;
adding polyethylene glycol to the polymeric solution to form polymeric grafts of polyethylene glycol along the styrenic block copolymer;
mixing at least one bioactive agent with the polymeric solution to form a drug-polymer solution;
applying the drug-polymer solution onto a stent framework; and
drying the drug-polymer solution.

23. The method of claim 22 wherein the pegylated styrenic block copolymer solvent is selected from the group consisting of chloroform, tetrahydrofuran, methyl chloride, toluene, ethyl acetate, dioxane, and a organic solvent.

24. The method of claim 22 further comprising:
adding an aliquot of maleic anhydride to the polymeric solution to initiate formation of the polymeric grafts.

25. The method of claim 22 wherein the drug-polymer solution is applied using an application technique selected from the group consisting of dipping, spraying, painting, and brushing.

26. The method of claim 22 wherein the drug-polymer solution is dried in a vacuum environment.

27. The method of claim 22 wherein the drug-polymer solution is dried at a temperature between 25 degrees centigrade and 45 degrees centigrade.

28. A drug-polymer coated stent, comprising:
a stent framework; and
a drug-polymer coating disposed on the stent framework, wherein the drug-polymer coating comprises a styrenic block copolymer grafted with polyethylene glycol; and
a bioactive drug dispersed within the drug-polymer coating.

29. The system of claim 28 wherein the stent framework comprises one of a metallic base or a polymeric base.

30. The system of claim 28 wherein the grafted styrenic block copolymer comprises a chain length of the styrenic block copolymer, a chain length of the polyethylene glycol grafts, and a polyethylene glycol based on a predetermined elution rate of the bioactive drug.

31. The system of claim 28 wherein the bioactive drug comprises a bioactive agent selected from the group consisting of an antirestenotic agent, an antisense agent, an antineoplastic agent, an antiproliferative agent, an anti-thrombogenic agent, an anticoagulant, an antiplatelet agent, an antibiotic, an anti-inflammatory agent, a steroid, a gene therapy agent, a therapeutic substance, an organic drug, a pharmaceutical compound, a recombinant DNA product, a recombinant RNA product, a collagen, a collagenic derivative, a protein, a protein analog, a saccharide, and a saccharide derivative.

32. The system of claim 28 further comprising:
a primer coating disposed on the stent framework between the stent framework and the drug-polymer coating.

33. The system of claim 32 wherein the primer coating is selected from the group consisting of parylene, polyurethane, phenoxy, epoxy, polyimide, polysulfone, pellathane, and a suitable polymeric primer material.

34. A method of treating a vascular condition, comprising:
   inserting a drug-polymer coated stent within a vessel of a body, the drug-polymer coated stent including at least one bioactive agent and a block copolymer grafted with polyethylene glycol; and
   eluting the bioactive agents from the drug-polymer coated stent into the body.

35. The method of claim 34 wherein the grafted styrenic block copolymer controls an elution rate of each bioactive agent.

36. The method of claim 34 further comprising:
   selecting the grafted styrenic block copolymer based on a predetermined elution rate of each bioactive agent.

* * * * *

UNITED STATES PATENT AND TRADEMARK OFFICE
CERTIFICATE OF CORRECTION

| | | |
|---|---|---|
| PATENT NO. | : 6,918,929 B2 | Page 1 of 1 |
| APPLICATION NO. | : 10/351156 | |
| DATED | : July 19, 2005 | |
| INVENTOR(S) | : Kishore Udipi et al. | |

It is certified that error appears in the above-identified patent and that said Letters Patent is hereby corrected as shown below:

Column, 12, line 24, "a organic solvent" should be changed to -- a suitable organic solvent --

Signed and Sealed this

Second Day of January, 2007

JON W. DUDAS
*Director of the United States Patent and Trademark Office*